US00PP34640P2

(12) United States Plant Patent
Ullrich

(10) Patent No.: US PP34,640 P2
(45) Date of Patent: Oct. 11, 2022

(54) ***OZOTHAMNUS* PLANT NAMED 'ESM RI009'**

(50) Latin Name: *Ozothamnus diosmifolius*
Varietal Denomination: ESM RI009

(71) Applicant: TECNOVIV LLC, Miami, FL (US)

(72) Inventor: Clarisse Ullrich, Quito (EC)

(73) Assignee: TECNOVIV LLC, Miami, FL (US)

( * ) Notice: Subject to any disclaimer, the term of this patent is extended or adjusted under 35 U.S.C. 154(b) by 0 days.

(21) Appl. No.: 17/669,267

(22) Filed: Feb. 10, 2022

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05); *A01H 5/02* (2013.01)

(58) Field of Classification Search
USPC ..... Plt./263.1
CPC ..... A01H 5/02
See application file for complete search history.

(56) References Cited

PUBLICATIONS

CPVO Application Consultation Version 4.1.51—Citation for 'ESM RI009'; Dec. 15, 2019; 1 page.*

* cited by examiner

*Primary Examiner* — Kent L Bell
(74) *Attorney, Agent, or Firm* — C. Anne Whealy

(57) ABSTRACT

A new and distinct cultivar of *Ozothamnus* plant named 'ESM RI009', characterized by its upright plant habit with relatively long flowering stems; vigorous growth habit; freely branching habit; freely flowering habit; flowers with dark pink-colored phyllaries arranged on compact and dense inflorescences; and good cut flower performance.

1 Drawing Sheet

Botanical designation: *Ozothamnus diosmifolius.*
Cultivar denomination: 'ESM RI009'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Tecnoviv LLC of Miami, Fla. on Oct. 18, 2019, application number 2019/2661. Foreign priority is not claimed to this European Community Plant Breeder's Rights application.

A Columbian Plant Breeder's Rights application for the instant plant was filed by the Applicant/Assignee of the instant application, Tecnoviv LLC of Miami, Fla. on Jun. 26, 2020, application number A202688. Foreign priority is not claimed to this Colombian Plant Breeder's Rights application.

An Ecuadorian Plant Breeder's Rights application for the instant plant was filed by the Applicant/Assignee of the instant application, Tecnoviv LLC of Miami, Fla. on Dec. 20, 2019, application number 1628-19. Foreign priority is not claimed to this Ecuadorian Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Ozothamnus* plant, botanically known as *Ozothamnus diosmifolius,* commonly referred to as Rice Flower or Sago Bush and hereinafter referred to by the name 'ESM RI009'.

The new *Ozothamnus* plant is a product of a planned breeding program conducted by the Inventor in El Quinche, Pichincha, Ecuador. The objective of the breeding program is to create new *Ozothamnus* plants that are suitable as cut flowers.

The new *Ozothamnus* plant originated from an open-pollination in April, 2009 of a proprietary *Ozothamnus* selection identified as Line R28, not patented, as the female, or seed, parent with an unknown *Ozothamnus* selection, as the male, or pollen, parent. The new *Ozothamnus* plant was discovered and selected by the Inventor as a single flowering plant within the progeny of the stated open-pollination in a controlled greenhouse environment in El Quinche, Pichincha, Ecuador in April, 2010.

Asexual reproduction of the new *Ozothamnus* plant by terminal cuttings in El Quinche, Pichincha, Ecuador since October, 2011 has shown that the unique features of this new *Ozothamnus* plant are stable and reproduced true to type in successive generations of asexual reproduction.

SUMMARY OF THE INVENTION

Plants of the new *Ozothamnus* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'ESM RI009'. These characteristics in combination distinguish 'ESM RI009' as a new and distinct *Ozothamnus* plant:

1. Upright plant habit with relatively long flowering stems.
2. Vigorous growth habit.
3. Freely branching habit.
4. Freely flowering habit.
5. Flowers with dark pink-colored phyllaries arranged on compact and dense inflorescences.
6. Good cut flower performance.

Plants of the new *Ozothamnus* differ primarily from plants of the female parent selection in plant height as plants of the new *Ozothamnus* are taller than plants of the female parent selection.

Plants of the new *Ozothamnus* can be compared to plants of *Ozothamnus diosmifolius* 'Victoria White', not patented. In side-by-side comparisons, plants of the new *Ozothamnus* differ primarily from plants of 'Victoria White' in plant height as plants of the new *Ozothamnus* are taller than plants of 'Victoria White'. In addition, plants of the new *Ozothamnus* have more rounded inflorescences than plants of 'Victoria White'.

BRIEF DESCRIPTION OF THE PHOTOGRAPH

The accompanying colored photographic sheet illustrates the overall appearance of the new *Ozothamnus* plant showing the colors as true as it is reasonably possible to obtain in colored reproductions of this type. Colors on the photograph sheet may differ slightly from the color values cited in the detailed botanical description which accurately describe the colors of the new *Ozothamnus* plant.

On the right of the photographic sheet is a side perspective view of a typical flowering stem of 'ESM RI009'.

At the upper left of the photographic sheet is a close-up view of typical flowers of 'ESM RI009'.

At the lower left of the photographic sheet is a close-up view of a typical inflorescence of 'ESM RI009'.

And at the center left of the photographic sheet are close-up views of the upper and lower surfaces of typical leaves of 'ESM RI009'.

DETAILED BOTANICAL DESCRIPTION

The aforementioned photographic sheet, following observations and measurements describe plants grown in ground beds in a outdoor nursery in Cayambe, Pichincha, Ecuador and under typical *Ozothamnus* production practices. Plants were one year and eleven months old when the photographs and the description were taken. During the production of the plants, day temperatures ranged from 17° C. to 21° C., night temperatures ranged from 5° C. to 8° C. and light levels averaged 19,338 lux. In the following description, color references are made to The Royal Horticultural Society Colour Chart, 2015 Edition, except where general terms of ordinary dictionary significance are used.

Botanical classification: *Ozothamnus diosmifolius* 'ESM RI009'.

Parentage:

*Female parent.*—Proprietary selection of *Ozothamnus diosmifolius* identified as Line R28.

*Male parent.*—Unknown selection of *Ozothamnus diosmifolius,* not patented.

Propagation:

*Type.*—Terminal vegetative cuttings.

*Time to initiate roots, summer.*—About two to three weeks at temperatures as high as 47° C.

*Time to produce a rooted cutting, summer.*—About six to eight weeks at temperatures as high as 47° C.

*Root description.*—Fine, fibrous; typically close to 161B in color, actual color of the roots is dependent on substrate composition, water quality, fertilizer type and formulation, substrate temperature and physiological age of roots.

*Rooting habit.*—Moderately freely branching habit; medium density.

Plant description:

*Plant and growth habit.*—Perennial plant appropriate to be grown as a cut flower; upright plant habit with relatively long flowering stems; vigorous growth habit and rapid growth rate; freely branching habit with up to four primary branches each with up to three secondary branches developing per plant.

*Plant height.*—About 159.1 cm.

*Plant diameter or spread.*—About 59.3 cm.

*Lateral branches.*—Length: About 120.5 cm. Diameter: About 6 mm. Internode length: About 6 mm. Strength: Moderately strong to strong. Texture and luster: Pubescent; matte. Color, developing: Close to 144B. Color, developed: Close to 146C and 176B.

Leaf description:

*Arrangement.*—Alternate, simple; sessile.

*Length.*—About 1.7 cm.

*Width.*—About 0.8 mm.

*Shape.*—Linear.

*Apex.*—Acute to obtuse.

*Base.*—Attenuate to cordate.

*Margin.*—Entire.

*Texture and luster, upper surface.*—Rough, glandular; matte.

*Texture and luster, lower surface.*—Pubescent; matte.

*Venation pattern.*—Parallel.

*Color.*—Developing leaves, upper surface: Close to 143A. Developing leaves, lower surface: Close to 145B. Fully expanded leaves, upper surface: Close to 147A; venation, close to 147A. Fully expanded leaves, lower surface: Close to 147C; venation, close to 147C.

Inflorescence description:

*Arrangement and habit.*—Hemispherical inflorescences arranged in terminal and axillary compound corymbs; inflorescences face mostly upright; freely flowering habit, with about 332.5 flowers per inflorescences; ray floret development has not been observed on plants of the new *Ozothamnus.*

*Fragrance.*—Faintly fragrant; pleasant.

*Time to flower.*—Plants flower year-round in Ecuador.

*Flower longevity.*—Flowers maintain good substance for about 77 days on the plant and for about eight days as a cut flower; flowers persistent.

*Inflorescence buds.*—Height: About 2 mm. Diameter: About 1.1 mm. Shape: Rounded. Texture and luster: Smooth, glabrous; papery. Color: Close to 63A to 63C.

*Corymb diameter.*—About 34.8 cm.

*Corymb height.*—About 69.6 cm.

*Flower diameter.*—About 2 mm to 3 mm.

*Flower height.*—About 4 mm.

*Disc florets.*—Shape: Tubular; apex dentate. Length: About 1.5 mm. Diameter: About 0.45 mm. Texture, inner and outer surfaces: Smooth, glabrous. Color, inner surface: Close to 155B; venation, close to 155B. Color, outer surface: Close to 144D; venation, close to 144D.

*Phyllaries.*—Quantity and arrangement: About 36 arranged in about five to six whorls; imbricate. Length: About 3 mm. Width: About 2 mm. Shape: Ovate. Apex: Acute. Base: Truncate. Margin: Entire. Texture and luster, upper and lower surfaces: Smooth, glabrous, papery; matte. Color: When opening upper and lower surfaces: Close to 63A to 63C. Fully opened, upper and lower surfaces: Close to 63C and 155B; color becoming closer to 160B and 161A with subsequent development.

*Peduncles.*—Length. About 1.8 cm. Diameter: About 1 cm. Strength: Strong. Aspect: Upright to about 45° from lateral branch axis. Texture and luster: Pubescent; matte. Color: Close to 144B and 145B.

*Pedicels.*—Length: About 4.4 mm. Diameter: About 0.4 mm. Strength: Moderately strong. Aspect: About 45° to 85° from peduncle axis. Texture and luster: Pubescent; matte. Color: Close to 144B and 145B.

*Reproductive organs.*—Androecium: Quantity per disc floret: About five. Filament length: About 3.5 mm. Filament color: Close to 155A. Anther shape: Lanceolate. Anther length: About 1.5 mm. Anther color: Close to 155A. Pollen amount: Scarce. Pollen color: Close to 155A. Gynoecium: Quantity per disc floret: One. Pistil length: About 3.5 mm. Stigma diameter: About 1.5 mm. Stigma shape: Bi-parted. Stigma color: Close to 155A. Style length: About 3.5 mm. Style color: Close to 155A. Ovary color: Close to 145C. Seeds and fruits: To date, seed and fruit development have not been observed on plants of the new *Ozothamnus.*

Pathogen & pest resistance: To date, plants of the new *Ozothamnus* have not been shown to be resistant to pathogens and pests common to *Ozothamnus.*

Garden performance: Plants of the new *Ozothamnus* have been observed to tolerate rain, wind and temperatures ranging from 9° C. to 23° C.

It is claimed:

1. A new and distinct *Ozothamnus* plant named 'ESM RI009' as illustrated and described.

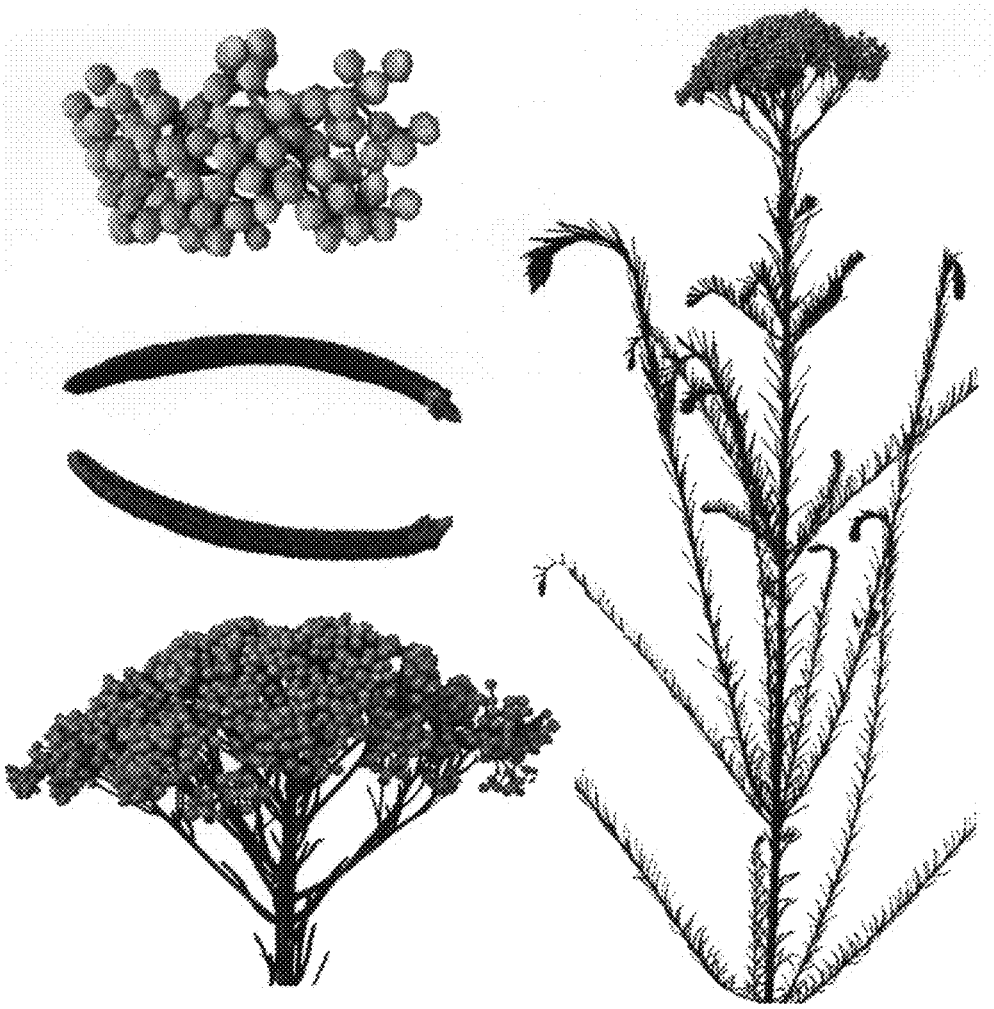

* * * * *